United States Patent [19]

Howard et al.

[11] Patent Number: 5,006,360

[45] Date of Patent: Apr. 9, 1991

[54] LOW CALORIE FAT SUBSTITUTE COMPOSITIONS RESISTANT TO LAXATIVE SIDE EFFECT

[75] Inventors: Norman B. Howard, Hilton Head Island, S.C.; David C. Kleinschmidt, Fairfield, Ohio

[73] Assignee: The Procter & Gamble Company, Cincinnati, Ohio

[21] Appl. No.: 211,802

[22] Filed: Jun. 27, 1988

[51] Int. Cl.[5] ............................................. A23L 1/307
[52] U.S. Cl. .................................... 426/601; 426/604; 426/61
[58] Field of Search ........................ 426/601, 604, 611

[56] References Cited

U.S. PATENT DOCUMENTS

| | | |
|---|---|---|
| 2,831,854 | 4/1958 | Tucker et al. . |
| 2,874,175 | 2/1959 | Feuge et al. . |
| 2,962,419 | 11/1960 | Minich . |
| 3,579,548 | 5/1971 | Whyte . |
| 3,600,186 | 8/1971 | Mattson et al. ........................ 426/603 |
| 3,932,532 | 1/1976 | Hunter et al. . |
| 3,963,699 | 6/1976 | Rizzi et al. . |
| 4,005,195 | 1/1977 | Jandacek .......................... 426/658 X |
| 4,005,196 | 1/1977 | Jandacek et al. ................ 426/658 X |
| 4,304,768 | 12/1981 | Staub et al. ........................... 426/558 |
| 4,341,807 | 7/1982 | Turbak et al. ........................ 426/570 |
| 4,374,702 | 2/1983 | Turbak et al. . |
| 4,378,381 | 3/1983 | Turbak et al. ........................ 426/576 |
| 4,461,782 | 7/1984 | Robbins et al. ....................... 426/549 |
| 4,481,076 | 11/1984 | Herrick ................................. 162/158 |
| 4,508,746 | 4/1985 | Hamm . |
| 4,517,360 | 5/1985 | Volpenhein . |
| 4,518,772 | 5/1985 | Volpenhein . |
| 4,582,715 | 4/1986 | Volpenhein . |
| 4,582,927 | 4/1986 | Fulcher ................................. 960/201 |
| 4,861,613 | 8/1989 | White ................................... 426/611 |
| 4,925,692 | 5/1990 | Ryan ..................................... 426/601 |

FOREIGN PATENT DOCUMENTS

| | | |
|---|---|---|
| 205273 | 12/1976 | European Pat. Off. . |
| 0233856 | 9/1987 | European Pat. Off. . |
| 0236288 | 9/1987 | European Pat. Off. . |
| 254547 | 1/1988 | European Pat. Off. . |
| 207070 | 2/1984 | Fed. Rep. of Germany . |

OTHER PUBLICATIONS

Turbak, "Microfibrillated Cellulose-A New Composition of Commercial Significance", Tappi, 1984, Non--Woven Symposium, p. 121.

Primary Examiner—Donald E. Czaja
Assistant Examiner—Drew S. Workman
Attorney, Agent, or Firm—Gary M. Sutter; John M. Howell; Richard C. Witte

[57] ABSTRACT

The present invention relates to low calorie fat substitute compositions that are useful as fat replacements in low calorie foods, and as pharmaceutical compositions. Sucrose fatty acid esters are preferred low calorie fat substitutes. The compositions are highly resistant to an undesirable laxative side effect. These benefits are achieved by formulating compositions comprising a liquid polyol fatty acid polyester, at least about 10% solid low calorie fat substitute by weight of the liquid polyester, and at least about 1% of a cohesive network of polysaccharide fibrils and microfibrils, for example microfibrillated cellulose, by weight of the liquid polyester.

23 Claims, 2 Drawing Sheets

Fig. 1

LOW CALORIE FAT SUBSTITUTE COMPOSITIONS RESISTANT TO LAXATIVE SIDE EFFECT

TECHNICAL FIELD

The present invention relates to the field of low calorie fat and oil substitutes. Specifically, the invention relates to low calorie fat substitute compositions that contain polysaccharide fibrils and microfibrils such as microfibrillated cellulose. The compositions are particularly useful as fat replacements in foods.

BACKGROUND OF THE INVENTION

The consumption of large amounts of triglyceride fats has been linked to various health problems. For example, one of the most common metabolic problems among people today is obesity. This condition is primarily due to ingestion of a greater number of calories than are expended. Fat is the most concentrated form of energy in the diet, with each gram of fat supplying approximately 9 calories, and triglyceride fats constitute about 90% of the total fat consumed in the average diet.

The National Institutes of Health Consensus Development Conference, "Lowering Blood Cholesterol to Prevent Heart Disease", JAMA, Vol. 253, No. 14, pp. 2080–2086 (1985), concluded that elevation of blood cholesterol levels is a major cause of coronary artery disease, and recommended a reduction in the amount of fat eaten to reduce blood serum cholesterol levels.

Hence, there is a need for ways to reduce the amount of triglyceride fats in the diet, in order to reduce the health risks associated with these fats.

Low calorie fats which can replace triglycerides are described by Mattson et al. in U.S. Pat. No. 3,600,186. Food compositions are disclosed in which at least a portion of the triglyceride content is replaced by a polyol fatty acid ester having at least four fatty acid ester groups with each fatty acid having from 8 to 22 carbon atoms.

Robbins et al. U.S. Pat. No. 4,461,782, issued July 24, 1984, discloses baked products containing 12-60% liquid polyol polyester and 25-85% microcrystalline cellulose and flour. Examples given are breads, cakes and wafers.

Mattson et al. U.S. Pat. No. 3,954,976 describes pharmaceutical compositions for inhibiting the absorption of cholesterol comprising effective unit dosage amounts of a polyol fatty acid ester having at least four fatty acid ester groups.

The esters disclosed in these patents are useful as fat substitutes in low calorie food products or in pharmaceutical compositions for controlling hypercholesterolemia. Unfortunately, regular ingestion of moderate to high levels of liquid polyol fatty acid polyesters can produce an undesirable laxative side effect, namely, leakage of the ester through the anal sphincter.

Jandacek et al. U.S. Pat. Nos. 4,005,195 and 4,005,196 describe a method of reducing the undesirable laxative side effect through the addition to the liquid polyesters of anti-anal leakage agents. The anti-anal leakage agents include solid fatty acids (melting point 37° C. or higher) and their triglyceride source, and solid polyol fatty acid polyesters.

Other patents describe the use of microfibrillated cellulose in foods. For example, Turbak et al. U.S. Pat. No. 4,341,807 issued July 27, 1982, describes food products containing a suspension of microfibrillated cellulose as a thickener, flavor carrier and suspension stabilizer. Food uses specifically taught include fillings, crushes, soups, gravies, puddings, dips, toppings and other food products.

Turbak, "Microfibrillated Cellulose—A New Composition of Commercial Significance," Tappi, 1984 Non-Woven Symposium, page 121, describes the use of microfibrillated cellulose in reduced calorie jams and jellies, reduced calorie foods, and low and reduced calorie spreads.

Neither of the Turbak references suggests that microfibrillated cellulose can be used to reduce laxative side effect of a liquid polyol polyester.

It is an object of the present invention to provide low calorie fat substitute compositions that are useful as a replacement for normal triglyceride fats in low calorie foods, and as pharmaceutical compositions.

It is another object of the present invention to provide low calorie fat substitute compositions that are resistant to an undesirable laxative side effect.

These and other objects of the present invention will become evident from the disclosure herein.

All parts, percentages, and ratios used herein are by weight unless otherwise indicated.

SUMMARY OF THE INVENTION

The present invention relates to low calorie fat substitute compositions that are useful as fat replacements in low calorie foods, and as pharmaceutical compositions. Sucrose fatty acid esters are preferred low calorie fat substitutes. The compositions are highly resistant to an undesirable laxative side effect. These benefits are achieved by formulating compositions comprising a liquid polyol fatty acid polyester, at least about 10% solid low calorie fat substitute by weight of the liquid polyester, and at least about 1% of a cohesive network of polysaccharide fibrils and microfibrils, for example of microfibrillated cellulose, by weight of the liquid polyester.

DETAILED DESCRIPTION OF THE INVENTION

The present invention is based on the discovery that when a network of polysaccharide fibrils and microfibrils is dispersed in a mixture of a liquid polyol fatty acid polyester and a solid low calorie fat substitute, the resulting composition is even more resistant to laxative side effect than the liquid/solid mixture alone. This finding was unexpected in view of the fact that no laxative side effect reduction is seen in the two-part combination of liquid polyester and fibrils and microfibrils.

The addition of the polysaccharide fibrils and microfibrils is thought to provide a material of high surface area which serves as nucleating sites for the precipitation of the solid fat substitute, thereby entrapping the liquid polyester in a matrix with a hydrophobic surface. Apparently the surface of the resultant gel has a high contact angle, and water is not readily able to spread or penetrate the surface and cause separation of the liquid polyester.

A low calorie fat substitute composition according to the present invention comprises a liquid polyol fatty acid polyester; at least about 10% solid low calorie fat substitute by weight of the liquid polyester; and at least about 1% of a cohesive network of polysaccharide fibrils and microfibrils by weight of the liquid polyester. Preferably, the composition comprises at least about 15% solid polyester by weight of the liquid polyester, and at least about 5% fibrils and microfibrils by weight of the liquid polyester.

A particularly preferred embodiment of the present invention is a composition comprising from about 60% to about 89% by weight liquid polyol fatty acid polyester, from about 10% to about 25% by weight solid low calorie fat substitute, and from about 1% to about 15% by weight of a cohesive network of polysaccharide fibrils and microfibrils. Most preferably, the composition comprises from about 70% to about 80% liquid polyester, from about 15% to about 20% solid fat substitute, and from about 5% to about 10% fibrils and microfibrils.

Liquid Polyol Fatty Acid Polyesters

The liquid polyol fatty acid polyesters of the present invention are liquids at body temperature, i.e., have a melting point of about 37° C. (98.6° F.) or below. In general, the liquid polyesters are those which are made from unsaturated fatty acids, whereas solid polyesters are substantially saturated.

The liquid polyesters comprise sugar fatty acid polyesters, sugar alcohol fatty acid polyesters, and mixtures thereof, the sugars and sugar alcohols containing from 4 to 8 hydroxyl groups. Sugar or sugar alcohol fatty acid polyesters comprise sugars or sugar alcohols, and fatty acids. The term "sugar" is used herein in its conventional sense as generic to mono- and disaccharides. The term "sugar alcohol" is also used in its conventional sense as generic to the reduction product of sugars wherein the aldehyde or ketone group has been reduced to an alcohol. The fatty acid ester compounds are prepared by reacting a monosaccharide, disaccharide or sugar alcohol with fatty acids as discussed below.

Examples of suitable monosaccharides are those containing 4 hydroxyl groups such as xylose, arabinose, and ribose; the sugar alcohol derived from xylose, i.e., xylitol, is also suitable. The monosaccharide erythrose is not suitable for the practice of this invention since it only contains 3 hydroxyl groups; however, the sugar alcohol derived from erythrose, i.e. erythritol, contains 4 hydroxyl groups and is thus suitable. Among 5 hydroxyl-containing monosaccharides that are suitable for use herein are glucose, mannose, galactose, fructose, and sorbose. A sugar alcohol derived from sucrose, glucose, or sorbose, e.g., sorbitol, contains 6 hydroxyl groups and is also suitable as the alcohol moiety of the fatty acid ester compounds. Examples of suitable disaccharides are maltose, lactose, and sucrose, all of which contain eight hydroxyl groups.

Preferred polyols for preparing the liquid polyesters for use in the present invention are selected from the group consisting of erythritol, xylitol, sorbitol, glucose and sucrose. Sucrose is especially preferred.

The polyol starting material having at least four hydroxyl groups must be esterified on at least four of the -OH groups with a fatty acid containing from about 8 to about 22 carbon atoms, and preferably from about 14 to about 18 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional or geometrical isomers. However, in order to provide the liquid polyol polyesters of the present invention, at least about half of the fatty acids incorporated into a polyester molecule must be unsaturated. Oleic and linoleic acids, and mixtures thereof, are especially preferred.

The liquid polyol fatty acid polyesters useful in this invention must contain at least four fatty acid ester groups. Polyol fatty acid polyester compounds that contain three or less fatty acid ester groups are digested in and the products of digestion are absorbed from the intestinal tract much in the manner of ordinary triglyceride fats, whereas the polyol fatty acid polyester compounds that contain four or more fatty acid ester groups are substantially non-digestible and consequently non-absorbable by the human body. It is not necessary that all of the hydroxyl groups of the polyol be esterified with fatty acid, but it is preferable that the polyol contain no more than three unesterified hydroxyl groups, and more preferable that it contain no more than two unesterified hydroxyl groups. Most preferably, substantially all of the hydroxyl groups of the polyol are esterified with fatty acid, i.e., the compound is substantially completely esterified. The fatty acids esterified to the polyol molecule can be the same or mixed (but, as noted above, a substantial amount of the unsaturated acid ester groups must be present to provide liquidity).

The following are non-limiting examples of specific liquid polyol fatty acid polyesters containing at least four fatty acid ester groups suitable for use in the present invention: sucrose tetraoleate, sucrose pentaoleate, sucrose hexaoleate, sucrose heptaoleate, sucrose octaoleate, glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, and mixtures thereof.

As noted above, highly preferred polyol fatty acid esters are those wherein the fatty acids contain from about 14 to about 18 carbon atoms.

The polyol fatty acid polyesters suitable for use herein can be prepared by a variety of methods known to those skilled in the art. These methods include: transesterification of the polyol with methyl, ethyl or glycerol fatty acid esters using a variety of catalysts; acylation of the polyol with a fatty acid chloride; acylation of the polyol with a fatty acid anhydride; and acylation of the polyol with a fatty acid, per se. As an example, the preparation of polyol fatty acid esters is described in U.S. Pat. Nos. 2,831,854, 3,963,699, 4,517,360 and 4,518,772 (all herein incorporated by reference).

Specific, but non-limiting, examples of the preparation of liquid polyol fatty acid esters suitable for use in the practice of this invention are as follows.

Erythritol tetraoleate—Erythritol and a five-fold molar excess of methyl oleate are heated at 180° C. (356° F.) under vacuum, with agitation, in the presence of sodium methoxide catalyst over two reaction periods of several hours each. The reaction product (predominately erythritol tetraoleate) is refined in petroleum ether and crystallized three times from several volumes of acetone at 1° C. (34° F.).

Xylitol pentaoleate—Xylitol and a five-fold molar excess of methyl oleate in dimethylacetamide (DMAC) solution are heated at 180° C. (356° F.) for five hours in the presence of sodium methoxide catalyst, under vacuum. During this time the DMAC is removed by distillation. The product (predominately xylitol pentaoleate) is refined in petroleum ether solution and, after being freed of petroleum ether, is separated as a liquid layer four times from acetone at about 1° C. (34° F.) and twice from alcohol at about 10° C. (50° F.).

Sorbitol hexaoleate is prepared by essentially the same procedure used to prepare xylitol pentaoleate except that sorbitol is substituted for xylitol.

Sucrose octaoleate is prepared by substantially the same procedure as that used to prepare erythritol tetraoleate except that sucrose is substituted for erythritol.

Solid Low Calorie Fat Substitutes

The low calorie fat substitute compositions of the present invention comprise at least about 10% solid low calorie fat substitute by weight of the liquid polyol fatty acid polyester. The solid fat substitute can be any of a variety of edible, wholly or partially nondigestible compounds which can replace triglyceride fats or oils. The solid fat substitute must be at least partially nondigestible so that it can remain in combination with the liquid polyester and the fibrils and microfibrils as the composition passes through the digestive tract.

By "partially nondigestible" is meant that at least about 30% of the fat substitute is not digested or absorbed by the body. Preferably the solid fat substitute is at least 70% nondigestible. Most preferably, the solid fat substitute is 100% nondigestible, and it passes through the digestive system substantially the same as when it was ingested.

A preferred solid fat substitute for use in the present invention is a solid polyol fatty acid polyester of the type described hereinabove under the liquid polyester section. The solid polyesters are solids at body temperature, i.e., have a melting point above about 37° C. (98.6° F.). In general, the solid polyol polyesters are esterified with more saturated than unsaturated fatty acids. These solid polyesters generally have an iodine value of about 12 or below.

Typical examples of edible, solid, non-absorbable, non-digestible polyol polyesters useful herein include sucrose octastearate, sucrose octapalmitate, sucrose heptastearate, xylitol pentastearate, galactose pentapalmitate, and the like, saturated polyol polyesters having at least four -OH groups esterified with $C_{10}$–$C_{22}$ saturated fatty acids.

Another type of solid fat substitute useful herein comprises fatty acid esters which are non-digestible by virtue of branching on the α-carbon atom of the fatty acid moiety. Such materials, which are well known in the chemical arts, include, for example, α-methyl and a,a-dimethyl $C_{10}$–$C_{18}$ fatty acid esters of lower alcohols such as ethanol and of polyols such as glycerol.

Minich U.S. Pat. No. 2,962,419 (polyhydric alcohol fatty acid esters) and White U.S. Pat. No, 4,861,613 (esterified epoxide-extended polyols), both incorporated by reference herein, disclose fat substitutes which may be solid or liquid depending on the fatty acid composition. Polyol fatty acid ethers can also be made that are solids at body temperature. Other solid fat substitutes are suitable for use herein provided they are solid at body temperature and at least partially nondigestible.

Polysaccharide Fibrils and Microfibrils

Figure 1:
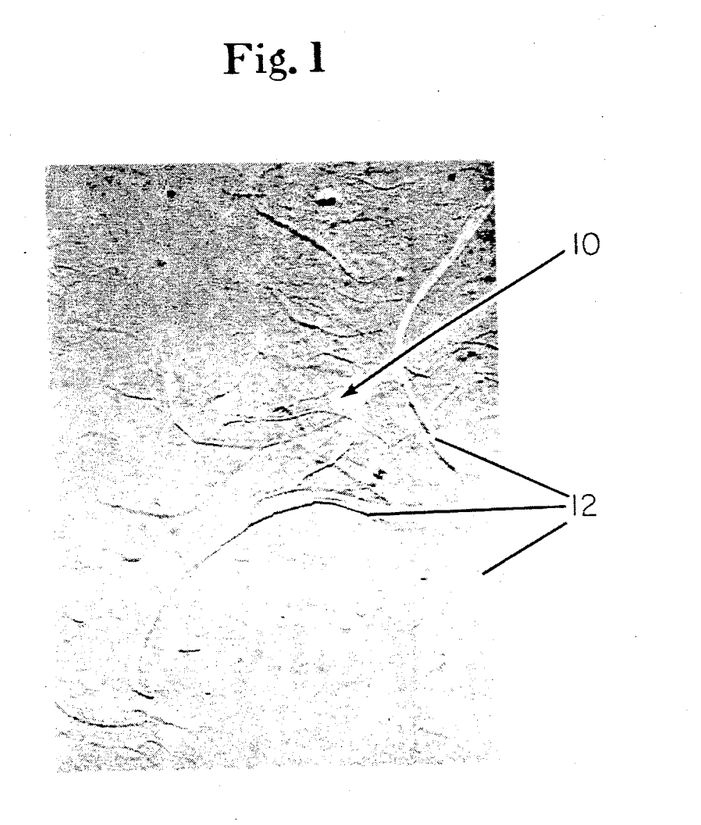
FIG. 1 is a photograph of a network of cellulosic fibrils and microfibrils taken at 500X magnification.

The third component of the present low calorie fat substitute compositions is a cohesive network of polysaccharide, substantially water-insoluble fibrils and microfibrils. This network is shown at a magnification of 500X in FIG. 1 and is indicated by numeral 10. At this magnification, only fibrils indicated by numeral 12 are visible. The microfibrils which are present in network 10 are visible only at magnifications much greater than 500X.

Figure 2:
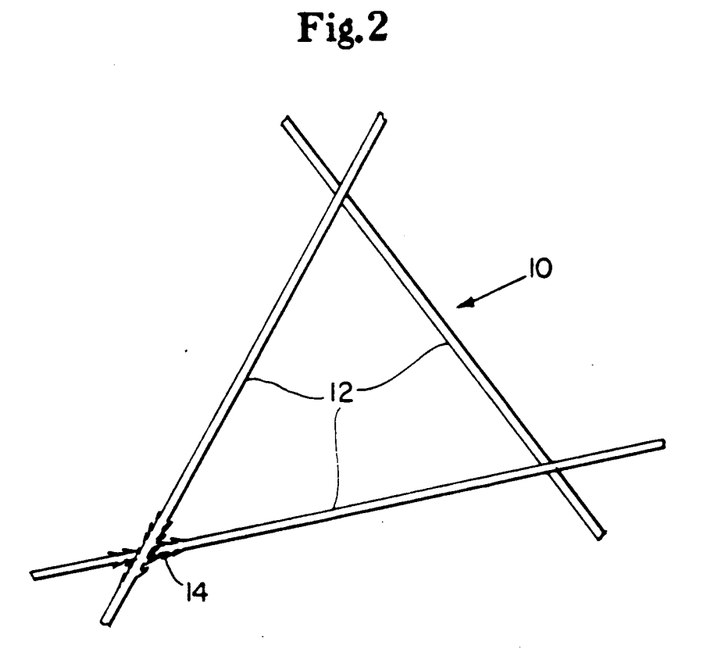
FIG. 2 is a greatly enlarged representation of what a portion of the network of cellulosic fibrils and microfibrils is believed to look like in the compositions of the present invention.

A representation of what a portion of network 10 is believed to look like, at a magnification much greater than 500X, is shown in FIG. 2. The fibrils which comprise this network are again indicated by numeral 12. The fibrils 12 basically constitute the "reinforcing rods" of network 10. The fibrils can vary in length, but are usually within the range of from about 10 to about 1,000 microns. The majority of these fibrils typically have a length of from about 100 to about 250 microns.

Fibrils 12 are comprised of rope-like bundles of microfibrils. The surface of the fibrils usually has exposed microfibrils which are indicated by numeral 14. It is believed that these exposed microfibrils 14 cause fibrils 12 to adhere together to form network 10. (It is believed that this adherence is due to hydrogen bonding between the fibrils and microfibrils.) Although the microfibrils are often still attached to the fibrils, it is believed that, in certain instances, unattached microfibrils can form portions of network 10.

The microfibrils also vary in length, but are generally shorter than the fibrils. Typically, the microfibrils have a length of from about 1 to about 100 microns. Another key difference between the fibrils and microfibrils is their diameter. Fibrils typically have a diameter of from about 0.1 to about 2 microns. By contrast, microfibrils typically have a diameter of from about 0.025 to about 0.1 microns.

This network of fibrils and microfibrils has a relatively large surface area. Generally, the surface area of this network is greater than about 100 m$^2$/g. Typically, the surface area of this network ranges from about 100 to about 170 m$^2$/g. This relatively large surface area is thought to be important to the laxative side effect reduction of the present invention.

The surface area of the fibrils and microfibrils is measured by a Quantasorb instrument (Quantachrome Company, Syosset, N.Y.). This measurement involves a monolayer nitrogen adsorption analysis of a dried sample at three different partial pressures, i.e. a three point B.E.T. analysis. The dried sample is obtained by drying an aqueous suspension of the fibrils and microfibrils with ethanol and acetone, followed by critical point drying with carbon dioxide. See Dawes, *Biological Techniques for Transmission and Scanning Electron Microscopy* (2d. Edition 1979), pp. 231–39, incorporated by reference herein, which describes techniques for critical point drying of materials.

The polysaccharide fibrils and microfibrils which form the cohesive network can be obtained from various sources. Cellulose is a preferred polysaccharide. A preferred source of cellulosic fibrils and microfibrils is microfibrillated cellulose prepared according to the method disclosed in Turbak et al U.S. Pat. No. 4,374,702, issued Feb. 22, 1983, which is incorporated herein by reference. In this method, cellulosic pulp or other unregenerated fibrous cellulose is added to a liquid suspending media which swells the cellulose. This liquid suspension is repeatedly passed through a small diameter orifice in which the mixture is subjected to a large pressure drop (at least 3,000 psi) and a high viscosity shearing action, followed by a high viscosity decelerating impact. This converts the cellulosic starting material into a suspension of microfibrillated cellulose. See also Herrick U.S. Pat. Nos. 4,481,076 and 4,481,077, issued Nov. 6, 1984, which disclose other methods for obtaining microfibrillated cellulose and which are incorporated herein by reference. Microfibrillated cellulose can also be obtained commercially from ITT Rayonier, a subsidiary of the assignee of these patents, as a spray-dried powder or moist cake.

The present invention is not limited by the method for making the fibrils and microfibrils. For example, it is thought that materials falling within the scope of the invention can also be made by a process of ball-milling cellulosic pulp.

Another method for obtaining cellulosic fibrils and microfibrils useful in the present invention is by bacterial fermentation of a sugar containing solution. Particularly suitable sugar containing solutions include coconut milk (Nata de Coco) or pineapple (Nata de Pina) solutions. A bacteria culture acts on the sugar solution to spin out a mat of cellulosic fibrils and microfibrils. This mat can then be redispersed in the present compositions to form the desired network of fibrils and microfibrils.

The polysaccharide fibrils and microfibrils of the invention can also be obtained through appropriate processing of other polysaccharide fiber sources, particularly cellulosic fibers. Such sources include fibrous fruits and vegetables, for example, orange pulp, strawberry pulp, apple pulp, and food fiber from other sources.

Processing methods capable of producing fibrils and microfibrils include other physical separation processes and fermentation processes. Other materials, for example, pectin, may be present in the fiber source, and these materials would be separated from the fibrils and microfibrils before use.

The polysaccharides can include other polysaccharidic materials besides cellulose. For example, it is thought that a network of fibrils and microfibrils for use in the present invention can be obtained by fungal fermentation of a glucose-containing solution to produce a 1,3-linked glucose-based polysaccharide.

Compositions Made with Preferred Polyesters

Certain sugar and sugar alcohol fatty acid polyesters, as described above in the section on liquid polyol polyesters, have been discovered that do not cause a laxative side effect even at relatively low levels of solids. These polyesters are characterized as having the following properties at 100° F. (37.8° C.): (a) a liquid/solid stability of at least about 50%, preferably at least about 70%; and (b) a solid fat content between about 5% and about 30%. Preferably the polyesters have a viscosity of at least about 1.0 poise, more preferably at least about 5.0 poise, after 10 minutes of steady shear at a shear rate of 10 seconds$^{-1}$. The methods of measuring viscosity and liquid/solid stability are described below in the Analytical Methods section.

These polyesters preferably have a solid fat content (SFC) at 100° F. (37.8° C.) between about 5% and about 25%, more preferably between about 10% and about 20%.

Therefore, a preferred embodiment of the present invention is a low calorie fat substitute composition as described hereinabove comprising a liquid polyester; at least about 10% solid low calorie fat substitute by weight of the liquid polyester; at least about 1% polysaccharide fibrils and microfibrils; and additionally comprising a sugar fatty acid polyester or sugar alcohol fatty acid polyester, or mixtures thereof, having the above-described stability, SFC, and preferably viscosity at 100° F. (37.8° C.).

Moreover, compositions can be made that are very resistant to laxative side effect even without the use of solid low calorie fat substitutes, if the compositions contain a sufficient amount of the above-described preferred polyesters. Hence, another embodiment of the present invention is a low calorie fat substitute composition comprising from about 1% to about 42% by weight liquid polyol fatty acid polyester; from about 1% to about 15% by weight of a cohesive network of polysaccharide fibrils and microfibrils; and from about 43% to about 98% by weight low calorie fat substitute selected from the group consisting of sugar fatty acid polyesters, sugar alcohol fatty acid polyesters, and mixtures thereof, the sugars and sugar alcohols containing from 4 to 8 hydroxyl groups, and each fatty acid group having from about 8 to about 22 carbon atoms, wherein the fat substitute has, at 100° F. (37.8° C.): (a) a liquid/solid stability of at least about 50%, preferably at least about 70%; and (b) a solid fat content between about 5% and about 30%. Preferably the polyesters have a viscosity of at least about 1 poise, more preferably at least about 5 poise, after 10 minutes of steady shear at a shear rate of 10 seconds$^{-1}$.

Highly preferred polyesters having the above-described properties are sucrose fatty acid polyesters. Preferred sucrose fatty acid polyesters have the majority of their hydroxyl groups esterified with fatty acids. Preferably at least about 85%, and most preferably at least about 95%, of the sucrose fatty acid polyesters are selected from the group consisting of octaesters, heptaesters and hexaesters, and mixtures thereof. Preferably, no more than about 35% of the esters are hexaesters or heptaesters, and at least about 60% of the sucrose fatty acid polyesters are octaesters. Most preferably, at least about 70% of the polyesters are octaesters. It is also most preferred that the polyesters have a total content of penta- and lower esters of not more than about 3%.

Preferably at least about 80%, and most preferably at least about 90%, of the fatty acids of the sucrose polyesters are selected from the group consisting of mixtures of palmitic, stearic, oleic, linoleic, and behenic acids. It is also most preferred that at least about 80% of the fatty acids are selected from the group consisting of mixtures of C16 to C18 fatty acids.

The fatty acids of the sucrose polyesters can be saturated, unsaturated, or mixtures thereof. The unsaturated fatty acids can include positional and geometric isomers (e.g., cis and trans isomers), or mixtures thereof.

More specifically, the following is a preferred fatty acid composition: from about 9% to about 12% palmitic; from about 35% to about 53% stearic; from about 19% to about 43% oleic; from about 2% to about 17% linoleic; from about 0% to about 2% linolenic; from about 0% to about 2% arachidic; from about 0% to about 10% behenic; and from about 0% to about 2% erucic.

Sucrose fatty acid polyesters having the above-described liquid/solid stability, solid fat content and viscosity can be made, for example, by esterifying sucrose with methyl esters of a fully hydrogenated soy oil (Iodine Value about 1) and a partially hydrogenated soy oil (Iodine Value about 107), blended in a 57:43 ratio.

Uses of the Low Calorie Fat Substitute Compositions

The present low calorie fat substitute compositions are useful in a wide variety of food and beverage products. For example, the compositions can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in Hong & Brabbs U.S. Pat. No. 4,455,333. The baked goods can contain fruit, cream, or other fillings. Other baked good uses include breads and rolls, crackers, pretzels, pancakes, waffles, ice cream cones and cups, yeast-raised baked goods, pizzas and pizza crusts, baked farinaceous snack foods, and other baked salted snacks.

The compositions can be used to make shortening and oil products, such as shortenings, margarines, spreads, butter blends, lards, cooking and frying oils, salad oils, popcorn oils, salad dressings, mayonnaise, and other edible oils.

The low calorie fat substitute compositions of the present invention can be fortified with vitamins and minerals, particularly the fat-soluble vitamins. The fat-soluble vitamins include vitamin A, vitamin D, vitamin E (tocopherol), and vitamin K. Four different tocopherols have been identified (alpha, beta, gamma and delta), all of which are oily, yellow liquids, insoluble in water but soluble in fats and oils. If desired, the compositions can be fortified with a recommended daily allowance (RDA), or increment or multiple of an RDA, of any of the fat-soluble vitamins or combinations thereof. The present compositions preferably contain about 1.1 mg. of Vitamin E as d-alpha tocopheryl acetate per 1000 grams of polyol polyester.

The present compositions are particularly useful in combination with particular classes of food and beverage ingredients. For example, an extra calorie reduction benefit is achieved when the compositions are used with noncaloric or reduced calorie sweeteners alone or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucralose; suosan; miraculin; monellin; sorbitol; xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

The compositions can be used in combination with other noncaloric or reduced calorie fats. Examples of such materials are: fatty alcohol esters of polycarboxylic acids (U.S. Pat. No. 4,508,746 of Hamm, assigned to CPC International, Inc., issued Apr. 2, 1985); fatty polyethers of polyglycerol (U.S. Pat. No. 3,932,532 of Hunter et al., assigned to ICI U.S., Inc., issued Jan. 13, 1976) (food use disclosed in German Patent 207,070, issued Feb. 15, 1984)); ethers and ether-esters of polyols containing the neopentyl moiety (U.S. Pat. No. 2,962,419 of Minich, issued Nov. 29, 1960); fatty alcohol diesters of dicarboxylic acids such as malonic and succinic acid (U.S. Pat. No. 4,582,927 of Fulcher, assigned to Frito-Lay, Inc., issued Apr. 15, 1986); triglyceride esters of alpha branched chain-alkyl carboxylic acids (U.S. Pat. No. 3,579,548 of Whyte, assigned to The Procter & Gamble Co., issued May 18, 1971); fatty acid diglyceride, diesters of dibasic acids (Feuge et al. U.S. Pat. No. 2,874,175); polyorganosiloxanes (European Patent Application 205,273 to Frye); and alpha-acylated: glycerides (Volpenhein U.S. Pat. No. 4,582,715), all above U.S. Patents incorporated herein by reference.

Other partial fat replacements useful in combination with the present compositions are medium chain triglycerides, highly esterified polyglycerol esters, acetin fats, plant sterol esters, N-Oil, polyoxyethylene esters, jojoba esters, mono/diglycerides of fatty acids, mono/-diglycerides of short-chain dibasic acids, silicone oils/-siloxanes (see, e.g., European Patent Application 205,273 of Dow Corp.), Simplesse (NutraSweet Co.), Olestrin (Reach Associates), and esterified epoxide-extended polyols (see U.S. Pat. No. 4,861,613 of Atlantic Richfield Co., incorporated by reference herein).

Bulking or bodying agents are useful in combination with the present compositions in many foods. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g. sorbitol and mannitol, and carbohydrates, e.g. lactose.

ANALYTICAL METHODS

I. Viscosity Measurement

A. Sample Preparation

The polyol fatty acid polyester sample is heated until it completely melts and is thoroughly mixed. Ten grams of the melted sample is weighed into a preheated 20 ml glass vial. The sample is then allowed to recrystallize at 100° F.±5° F. (37.8° C.±3+ C.) for 24 hours. After the 24 hour time period has elapsed, the sample is taken to the viscometer and the viscosity is measured.

B. Viscometer Operation Procedure

A Ferranti-Shirley plate and cone viscometer (Ferranti Electric, Inc., 87 Modular Ave., Commack, N.Y. 11725) equipped with a 600 g torque spring is used for the viscosity measurement. A cone is put into place, and the viscometer temperature is adjusted to 100° F. (37.8° C.). The chart recorder is calibrated, and the gap between the cone and plate is set. The cone speed is checked, and the cone and plate temperatures are equilibrated to 100° F. (37.8° C.). The panel controls are set. Sufficient sample is placed between the plate and the cone so that the gap is completely filled. The temperature is allowed to stabilize at 100° F. (37.8° C.) for about 30 seconds. Start the test by selecting the RPM for 10 seconds$^{-1}$ shear rate and record on the strip chart recorder. Record the shear stress at the maximum value for to and then for two 30-second intervals, followed by every minute thereafter until the value at 10 minutes is recorded. Viscosity (poise)=shear stress (dynes/cm$^2$) divided by shear rate (second$^{-1}$).

II. Liquid/Solid Stability Measurement

A polyol fatty acid polyester sample is heated until it completely melts and is thoroughly mixed. The sample is then poured into Beckman #344062 4.4 ml tubes to capacity. The tubes are immediately transferred to a 100° F.±5° F. (37.8° C.±3° C.) constant temperature room and allowed to recyrstallize undisturbed for 24 hours. The samples are then centrifuged at 60,000 in a Beckman Model L870M centrifuge having a Beckman Model SW60 maximum head (Beckman Instruments, Palo Alto, Calif.) rpm for one hour at 100° F. (37.8° C.). The force on the samples is 485,000 g's (i.e., the force at the bottom of the centrifuge tubes). The percent liquid separated is then measured by comparing the relative heights of the liquid and solid phases. Liquid/solid stability (%)=100×(total volume of sample−volume of liquid that separated)/total volume of sample.

III. Solid Fat Content Measurement

Before determining SFC values, the polyol fatty acid polyester sample is heated to a temperature of 158° F. (70° C.) or higher for at least 0.5 hours or until the sample is completely melted. The melted sample is then tempered at a temperature of 40° F. (4.4° C.) for at least 72 hours. After tempering, the SFC value of the polyester at a temperature of 100° F. (37.8° C.) is determined by pulsed nuclear magnetic resonance (PNMR). The method for determining SFC values by PNMR is described in Madison and Hill, *J. Amer. Oil Chem. Soc.*, vol 55 (1978), pp. 328-31 (herein incorporated by reference). Measurement of SFC by PNMR is also described in A.O.C.S. Official Method Cd. 16-81, *Official Methods and Recommended Practices of The American Oil Chemists Society*, 3rd Edition, 1987 (herein incorporated by reference).

The following examples are intended only to further illustrate the invention and are not intended to limit the scope of the invention which is defined by the claims.

EXAMPLE 1

A sucrose fatty acid polyester composition is prepared by combining liquid sucrose polyester, solid sucrose polyester, and microfibrillated cellulose:

| Ingredients | wt. | % |
| --- | --- | --- |
| Liquid sucrose polyester* | 164 g. | 76% |
| Solid sucrose polyester** | 37 g. | 17% |
| Microfibrillated cellulose*** | 15 g. | 7% |

*Sucrose octaoleate, iodine value 107
**Mixed hexa-, hepta- and octaesters of sucrose esterified with mixed soybean oil fatty acids, and hydrogenated to an iodine value of 8
***Microfibrillated cellulose, ITT Rayonier Forest Products The solid sucrose polyester is added to the liquid sucrose polyester, and the mixture is heated to about 160°-170° F. (71°-77° C.). The mixture is maintained at this temperature for about 15 minutes, with frequent stirring. While continuing to maintain the temperature, the microfibrillated cellulose fibers are then dispersed in the polyester mixture by slow addition using a standard kitchen mixer set at low speed, to make a uniform dispersion. The composition is then cooled rapidly by placing the mixing bowl into an ice water bath, and mixing at low speed until the dispersion is again uniform. Lastly, the composition is placed in a sealed glass jar and blanketed with nitrogen for storage.

The composition is very resistant to laxative side effect after ingestion.

EXAMPLE 2

Three kinds of sucrose fatty acid polyester compositions are made and tested for laxative side effect:

| Ingredients | % |
| --- | --- |
| Composition A: | |
| Liquid sucrose polyester* | 94% |
| Microfibrillated cellulose*** | 6% |
| Composition B: | |
| Liquid sucrose polyester* | 76% |
| Solid sucrose polyester** | 24% |
| Composition C: | |
| Liquid sucrose polyester* | 76% |
| Solid sucrose polyester** | 17% |
| Microfibrillated cellulose*** | 7% |

*Sucrose octaoleate, iodine value 107
**Mixed hexa-, hepta- and octaesters of sucrose esterified with mixed soybean oil fatty acids, and hydrogenated to an iodine value of 8
***Microfibrillated cellylose, ITT Rayonier Forest Products Composition A is found to be ineffective in laxative side effect reduction. Laxative side effect is reduced in both Composition B and Composition C, but Composition C is found to be an improvement over Composition B. It is concluded that the three part mixture of liquid sucrose polyester, solid sucrose polyester and microfibrillated cellulose is more resistant to laxative side effect than the two part mixture of liquid and solid sucrose polyester, and much more resistant than the two part mixture of liquid sucrose polyester and microfibrillated cellulose.

EXAMPLE 3

A composition is made as in Example 1, except that the composition contains 46% liquid sucrose polyester, 7% microfibrillated cellulose, and 47% of a sucrose fatty acid polyester made by esterifying sucrose with methyl esters of a fully hydrogenated soy oil (IV about 1) and a partially hydrogenated soy oil (IV about 107), blended in a 47:53 ratio. The latter sucrose polyester has the following properties:

| | |
| --- | --- |
| Viscosity After 10 min. steady shear at shear rate of 10 seconds$^{-1}$ | 25.9 poise |
| Liquid/Solid Stability | 92.5% |
| SFC at 100° F. (37.8° C.) | 10% |
| Fatty Acid Composition | |
| $C_{16}$ | 9.8% |
| $C_{16:1}$ | — |
| $C_{18}$ | 50.6 |
| $C_{18:1}$ | 21.6 |
| $C_{18:2}$ | 15.7 |
| $C_{18:3}$ | 1.0 |
| Others | 1.3 |
| Iodine Value | 48.6 |
| Ester Distribution | |
| Octa | 89.1% |
| Hepta | 10.9 |
| Hexa | <0.1 |
| Penta | <0.1 |
| Lower | <0.1 |

What is claimed is:

1. A low calorie fat substitute composition resistant to laxative side effect comprising: (i) a liquid polyol fatty acid polyester, (ii) at least about 10% solid low calorie fat substitute by weight of the liquid polyol fatty acid polyester, and (iii) at least about 1% of a cohesive network of polysaccharide fibrils and microfibrils by weight of the liquid polyol fatty acid polyester.

2. A composition according to claim 1 comprising at least about 15% solid low calorie fat substitute by weight of the liquid polyol fatty acid polyester.

3. A composition according to claim 1 comprising at least about 5% polysaccharide fibrils and microfibrils by weight of the liquid polyol fatty acid polyester.

4. A composition according to claim 1 comprising from about 60% to about 89% by weight liquid polyol fatty acid polyester, from about 10% to about 25% by weight solid low calorie fat substitute, and from about 1% to about 15% by weight polysaccharide fibrils and microfibrils.

5. A composition according to claim 4 comprising from about 70% to about 80% liquid polyol fatty acid polyester, from about 15% to about 20% solid low calorie fat substitute, and from about 5% to about 10% polysaccharide fibrils and microfibrils.

6. A composition according to claim 1 wherein the liquid polyol fatty acid polyester is selected from the group consisting of sugar fatty acid polyesters and sugar alcohol fatty acid polyesters, and mixtures thereof, wherein the sugars and sugar alcohols contain from 4 to 8 hydroxyl groups, wherein the sugar and sugar alcohol fatty acid polyesters are esterified with at least 4 fatty acid groups, and wherein each fatty acid group has from about 8 to about 22 carbon atoms.

7. A composition according to claim 6 wherein the liquid polyol fatty acid polyester is a sucrose fatty acid polyester.

8. A composition according to claim 1 wherein the solid low calorie fat substitute is selected from the group consisting of sugar fatty acid polyesters and sugar alcohol fatty acid polyesters, and mixtures thereof, wherein the sugars and sugar alcohols contain from 4 to 8 hydroxyl groups, wherein the sugar and sugar alcohol fatty acid polyesters are esterified with at least 4 fatty acid groups, and wherein each fatty acid group has from about 8 to about 22 carbon atoms.

9. A composition according to claim 8 wherein the solid low calorie fat substitute is a sucrose fatty acid polyester.

10. A composition according to claim 1 wherein the cohesive network of polysaccharide fibrils and microfibrils has a surface area of from about 100 to about 170 m$^2$/g.

11. A composition according to claim 1 wherein the polysaccharide fibrils and microfibrils are cellulosic fibrils and cellulosic microfibrils.

12. A composition according to claim 11 wherein the polysaccharide fibrils and microfibrils are microfibrillated cellulose.

13. A composition according to claim 1 wherein the polysaccharide fibrils and microfibrils are obtained by bacterial fermentation of a sugar-containing solution selected from the group consisting of coconut milk solution and pineapple solution, and mixtures thereof.

14. A composition according to claim 1 additionally comprising a liquid/solid stable low calorie fat substitute selected from the group consisting of sugar fatty acid polyesters, sugar alcohol fatty acid polyesters, and mixtures thereof, wherein the sugars and sugar alcohols contain from 4 to 8 hydroxyl groups, wherein the sugar and sugar alcohol fatty acid polyesters are esterified with at least 4 fatty acid groups, wherein each fatty acid group has from about 8 to about 22 carbon atoms, and wherein the liquid/solid stable low calorie fat substitute has, at 100° F. (37.8° C.):
(a) a liquid/solid stability of at least about 50%; and
(b) a solid fat content between about 5% and about 30%.

15. A low calorie fat substitute composition resistant to laxative side effect comprising: (i) from about 1% to about 42% by weight liquid polyol fatty acid polyester; (ii) from about 1% to about 15% by weight of a cohesive network of polysaccharide fibrils and microfibrils; and (iii) from about 43% to about 98% by weight liquid/solid stable low calorie fat substitute selected from the group consisting of sugar fatty acid polyesters, sugar alcohol fatty acid polyesters, and mixtures thereof, wherein the sugars and sugar alcohols contain from 4 to 8 hydroxyl groups, wherein the sugar and sugar alcohol fatty acid polyesters are esterified with at least 4 fatty acid groups, wherein each fatty acid group has from about 8 to about 22 carbon atoms, and wherein the liquid/solid stable low calorie fat substitute has, at 100° F. (37.8° C.):
(a) a liquid/solid stability of at least about 50%; and
(b) a solid fat content between about 5% and about 30%.

16. A composition according to claim 15 wherein the liquid polyol fatty acid polyester is a sucrose fatty acid polyesters, wherein the sucrose fatty acid polyester is esterified with at least 4 fatty acid ester groups, and wherein each fatty acid group has from about 8 to about 22 carbon atoms.

17. A composition according to claim 15 wherein the liquid/solid stable low calorie fat substitute is a sucrose fatty acid polyester.

18. A composition according to claim 15 wherein the cohesive network of polysaccharide fibrils and microfibrils has a surface area of from about 100 to about 170 m$^2$/g.

19. A composition according to claim 15 wherein the polysaccharide fibrils and microfibrils are cellulosic fibrils and cellulosic microfibrils.

20. A composition according to claim 19 wherein the polysaccharide fibrils and microfibrils are microfibrillated cellulose.

21. A composition according to claim 15 wherein the polysaccharide fibrils and microfibrils are obtained by bacterial fermentation of a sugar-containing solution selected from the group consisting of coconut milk solution and pineapple solution, and mixtures thereof.

22. A composition according to claim 1 wherein the polysaccharide fibrils and microfibrils are obtained by fungal fermentation of a glucose-containing solution.

23. A composition according to claim 15 wherein the polysaccharide fibrils and microfibrils are obtained by fungal fermentation of a glucose-containing sucrose.

* * * * *

REEXAMINATION CERTIFICATE (1690th)

United States Patent [19]

Howard et al.

[11] B1 5,006,360

[45] Certificate Issued  Apr. 28, 1992

[54] LOW CALORIE FAT SUBSTITUTE COMPOSITIONS RESISTANT TO LAXATIVE SIDE EFFECT

[75] Inventors: Norman B. Howard, Hilton Head Island, S.C.; David C. Kleinschmidt, Fairfield, Ohio

[73] Assignee: The Proctor & Gamble Company, Cincinnati, Ohio

Reexamination Request:
No. 91/002,423, Aug. 29, 1991

Reexamination Certificate for:
Patent No.: 5,006,360
Issued: Apr. 9, 1991
Appl. No.: 211,802
Filed: Jun. 27, 1988

[51] Int. Cl.$^5$ .............................................. A23L 1/307
[52] U.S. Cl. .................................... 426/601; 426/604; 426/611

[56] References Cited

U.S. PATENT DOCUMENTS 4,774,095  9/1988  Kleinschmidt et al. ............... 426/94
4,962,092  10/1990  Wood, Jr. .............................. 514/23

Primary Examiner—Donald E. Czaja

[57] ABSTRACT

The present invention relates to low calorie fat substitute compositions that are useful as fat replacements in low calorie foods, and as pharmaceutical compositions. Sucrose fatty acid esters are preferred low calorie fat substitutes. The compositions are highly resistant to an undesirable laxative side effect. These benefits are achieved by formulating compositions comprising a liquid polyol fatty acid polyester, at least about 10% solid low calorie fat substitute by weight of the liquid polyester, and at least about 1% of a cohesive network of polysaccharide fibrils and microfibrils, for example microfibrillated cellulose, by weight of the liquid polyester.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-23 is confirmed.